United States Patent [19]
Foslien

[11] Patent Number: 4,519,532
[45] Date of Patent: May 28, 1985

[54] STAPLER INCLUDING RATCHET MEANS FOR PREVENTING DOUBLE FEEDING OF STAPLES

[75] Inventor: Floyd L. Foslien, Stillwater, Minn.

[73] Assignee: Minnesota Mining and Manufacturing Company, Saint Paul, Minn.

[21] Appl. No.: 470,066

[22] Filed: Feb. 28, 1983

[51] Int. Cl.³ .................... A61B 17/04; B25C 5/02
[52] U.S. Cl. .......................................... 227/8; 227/19; 227/121; 227/DIG. 1
[58] Field of Search ............ 128/334 R; 227/19, 120, 227/121, 156, DIG. 1, 8

[56] References Cited

U.S. PATENT DOCUMENTS

| | | | |
|---|---|---|---|
| 2,289,308 | 7/1942 | Fancher et al. | 227/121 |
| 3,873,016 | 3/1975 | Fishbein | 227/83 |
| 4,077,557 | 3/1978 | Green | 227/83 |
| 4,185,762 | 1/1980 | Froehlich | 227/138 |
| 4,202,480 | 5/1980 | Annett | 227/8 |

FOREIGN PATENT DOCUMENTS

WO80/00230 2/1980 PCT Int'l Appl. .
2014503 8/1979 United Kingdom .

OTHER PUBLICATIONS

U.S. patent application Ser. No. 299,068 filed Sep. 3, 1981, in the name of Kent R. Struble, entitled "Stapler."

*Primary Examiner*—Paul A. Bell
*Attorney, Agent, or Firm*—Donald M. Sell; James A. Smith; William L. Huebsch

[57] ABSTRACT

A medical stapler including a ram adapted to push a staple along a passageway from an inlet opening into which staples are fed, to an outlet opening where the staple is closed about an anvil portion. A manually activated drive mechanism is adapted to move the ram and staple from the inlet to the outlet opening, and a slidable and pivotable pawl adapted for ratcheting engagement with the ram is provided to prevent reverse movement of the ram until the ram is moved to close the staple.

7 Claims, 14 Drawing Figures

STAPLER INCLUDING RATCHET MEANS FOR PREVENTING DOUBLE FEEDING OF STAPLES

TECHNICAL FIELD

This invention relates to mechanisms for preventing a second staple from being fed from a stack of staples into a mechanism for driving staples until a staple already in the mechanism is ejected.

BACKGROUND ART

Many staplers are known of the type comprising a housing having a passageway extending from an inlet opening to an outlet opening, which passageway is adapted to guide a single open staple from the inlet to the outlet opening; means for biasing a stack of open staples into the inlet opening; a ram slidably mounted on the housing for movement between a load position spaced from the inlet opening to afford movement of one of the open staples into the passageway, along the passageway with an end portion of the ram pushing the staple to an eject position at which the staple has been pushed to the outlet opening; and a manually activated drive mechanism for propelling the ram from its load to its eject position in opposition to biasing means. Typically, portions of the ram cover the inlet opening to prevent another staple from being fed into the passageway as the ram moves a staple in the channel toward the outlet opening, and means are provided for preventing movement of the ram back to its load position before it has moved fully to its eject position. Without such means, if the drive means was not completely activated to cause the ram to eject the staple from the outlet opening the ram could return to its load position under the influence of the biasing means, a second staple could enter the passageway, and upon subsequent activation of the drive mechanism the two staples in the passageway could jam the stapler.

While many prior art devices have been devised to prevent such double feeding, many are not as simple, inexpensive, or reliable as is desired.

DISCLOSURE OF THE INVENTION

The present invention provides a stapler which has a simple, reliable and inexpensive means for preventing reverse movement of a ram and thereby preventing a second staple from being fed through an inlet opening into a passageway for guiding staples through the stapler before a staple already in the passageway is moved to an outlet opening (called "double feeding" herein), even though activation of a drive mechanism for the stapler is terminated prior to moving the staple already in the passageway to the outlet opening.

According to the present invention there is provided a stapler generally of the type described above comprising a housing having a passageway extending from an inlet opening to an outlet opening at an end of the housing, which openings and passageway are adapted to guide a single staple moved from the inlet to the outlet opening. Means are provided for biasing a stack of open staples into the inlet opening, along with a ram mounted on the housing for sliding movement between (1) a load position with the ram spaced from the inlet opening to afford movement of one of the open staples into the passageway, (2) along the passageway with an end portion of the ram pushing the staple, (3) to an eject position at which the ram has pushed the staple to the outlet opening. The ram has a length adapted so that a portion thereof will be positioned adjacent the inlet opening during its movement from its load to its eject position to prevent movement of a staple into the passageway through the inlet opening, and drive means adapted for manual activation are provided to move the ram along the passageway, thereby moving one of the staples from the inlet opening through the passageway and to the outlet opening. Also, means are provided for biasing the ram toward its load position.

The novel means in the stapler according to the present invention for preventing movement of the ram toward its load position from a position intermediate its load and eject positions until the ram has been moved fully to its eject position comprises: (1) an elongate pawl including front and rear portions and a tooth projecting from one side; (2) surfaces on the ram defining an elongate recess adapted to receive the tooth, which surfaces include a front surface adjacent the front portion of the ram and a rear surface defining the end of the recess opposite the front surface; and (3) mounting means mounting the pawl on the housing generally parallel with the ram with its front portion adjacent the outlet opening and its tooth in the recess in the ram for longitudinal sliding movement from (1) an engage position at which the pawl is positioned with the front surface of the recess contacting the tooth when the ram is in the load position, and at which the pawl is positioned during movement of the ram a substantial portion of the distance toward the eject position until the rear surface of the recess contacts the tooth, (2) to a lockout position more closely adjacent the outlet opening than the initial position to which the pawl is moved by contact between the rear surface of the recess and the tooth during a final portion of the movement of the ram to the eject position, and at which the pawl is maintained during a major portion of the movement of the ram back to the load position, and (3) back to the engage position to which the pawl is moved by contact between the front surface of the recess and the tooth during a final portion of movement of the ram from the eject back to the load position. Means are provided for biasing the tooth toward the recess, and surface means including at least one abutment surface on the tooth and latching surfaces defining the recess between the front and rear surfaces are provided for affording, when the abutment and latching surfaces are in engagement, movement of the ram toward the eject position while preventing movement of the ram toward the load position; together with means for affording engagement of the abutment surface of the tooth with the latching surface of the recess under the influence of the biasing means when the pawl is in the engage position, for moving the abutment and latching surfaces out of engagement as the pawl is moved from the engage to the lockout position, and for maintaining the abutment and latching surfaces out of engagement when the pawl is in the lockout position.

In one embodiment the latching surfaces help to define a plurality of notches along the bottom of the recess adapted to be ratcheted along by the end of the tooth and to be engaged by a transverse abutment surface at the end of the tooth. In another embodiment the latching surfaces define opposite sides of the recess and are tapered toward the front surface of the recess, and the tooth has opposite tapered abutment surfaces along its sides that engage the latching surfaces as the tooth moves further into the recess under the influence of the biasing means during movement of the ram from its load to its eject positions.

In its preferred embodiment the stapler is adapted for medical use to join disunited tissue. The stapler housing has an anvil portion at the outlet opening adapted to engage the central portion of the staple. The staple will be closed around the anvil portion by the end portion of the ram as the ram moves the staple fully to its eject position so that the ends of the staple can engage portions of disunited tissue adjacent the outlet opening as the staple closes.

BRIEF DESCRIPTION OF THE DRAWING

The present invention will be more thoroughly explained with reference to the accompanying drawing where like numbers refer to like parts in the several views, and wherein.

DETAILED DESCRIPTION

Figure 1:
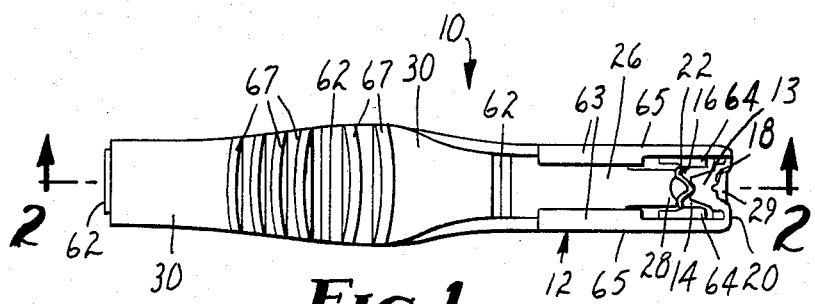
FIG. 1 is a top view of a stapler according to the present invention.

Referring now to FIGS. 1 through 11 of the drawing, there is shown a stapler 10 including a first embodiment of means according to the present invention for preventing double feeding of staples.

The stapler 10 comprises a housing 12 having a passageway 14 partially defined by a planar surface 13 extending from an inlet opening 16 to an outlet opening 18 at an end 20 of the housing 12, which passageway 14 is adapted to guide a single open staple 22 moved from the inlet opening 16 to the outlet opening 18; means for biasing a stack 24 of the open staples 22 into the inlet opening 16; and a ram 26 mounted on the housing 12 for sliding movement (1) from a load position (FIGS. 1, 2 and 3) with the ram 26 spaced from the inlet opening 16 to afford movement of one of the staples 22 into the passageway 14, (2) along the passageway 14 with an end portion 28 of the ram 26 pushing the staple 22 (FIGS. 4, 5 and 6), and (3) to an eject position (FIG. 7) at which the ram 26 has pushed the staple 22 to the outlet opening 18 and formed the staple 22 around an anvil portion 29 of the housing 12 projecting across the outlet opening 18. The stapler 10 illustrated is particularly adapted for use by surgeons to join disunited skin into which the ends of the staples 22 formed around the anvil portion 29 are clenched, after which the anvil portion 29 can be retracted from the central portion of the clenched staple 22; which type of stapling is well known in the art.

The ram 26 has a length adapted so that a portion of the ram 26 will always be positioned adjacent the inlet opening 16 during movement of the ram 26 from its load to its eject position to prevent movement of the adjacent staple 22 in the stack 24 into the passageway 14 through the inlet opening 16 until the staple 22 already in the passageway 14 is ejected. Drive means manually activatable by pressing a toggle joint linkage including two drive members 30 toward the housing 12 is provided for propelling the ram 26 (pivotally coupled to an adjacent end of one of the drive members 30) along the passageway 14 from its load to its eject position. A generally U-shaped end portion 34 of a spring 35 is positioned between the housing 12 and the adjacent drive member 30 to provide means for biasing the ram 26 toward and returning the ram 26 to its load position.

The means in the stapler 10 for preventing double feeding of staples 22 includes means for preventing movement of the ram 26 toward its load position from a position intermediate its load and eject positions until the ram 26 has been moved fully to its eject position. These means comprise: (1) an elongate pawl 38 including front and rear portions 39 and 40, and a tooth 41 projecting from one side between the front and rear portions 39 and 40, which tooth 41 has a transverse abutment surface 42 adjacent the front portion 39 and a rear surface 43 adjacent the rear portion 40; (2) surfaces on the ram 26 defining an elongate recess 46 adapted to receive the tooth 41, which surfaces include a front surface 47 adjacent the front portion 39 of the ram 26 adapted to abut the abutment surface 42 of the tooth 41, a rear surface 48 defining the end of the recess 46 opposite the front surface 47, and surfaces comprising latching surfaces 50 generally parallel to the front surface 47 defining a plurality of notches along the bottom of the recess 46 adapted to receive the end of tooth 41 with the abutment surface 42 of the tooth 41 abutting the latching surface 50 of the notch in which it is received; and (3) mounting means mounting the pawl 38 on the housing 12 generally parallel with the ram 26 with its front portion 39 adjacent the outlet opening 18 and its tooth 41 in the recess 46 in the ram 26 for longitudinal sliding and pivotal movement. These mounting means comprise means for biasing the tooth 41 toward the recess 46 provided by a central cantilevered portion 51 of the spring 35, and a ledge 52 formed on the housing 12 projecting generally parallel to the ram 26 away from the end 20 of the housing 12, which ledge 52 has a support surface 53 on its side opposite the ram 26. At least the rear surface 43 on the tooth 41 or the rear surface 48 defining the recess 46 and corresponding surfaces defining the notches (and as illustrated, all of these surfaces) are inclined to cam the tooth 41 out of the notches and to cam the tooth 41 out of the recess 46 when the rear surface 48 defining the recess 46 moves into engagement with the tooth 41. Thus, as the ram 26 is moved from its load to its eject position and back to its load position, the pawl 38 sequentially (1) is in an engage position (FIGS. 2 and 3) with the tooth 41 in the recess 46 and the front surface of the recess 46 contacting the abutment surface 42 of the tooth 41 so that the means for biasing the ram 26 to its load position will press shoulders 54 on the rear portion 40 of the pawl 38 against walls on the housing 12 to define the load portion for the ram 26, (2) is pivoted about the shoulders 54 to move along the surfaces defining the notches (FIGS.

Figure 2:
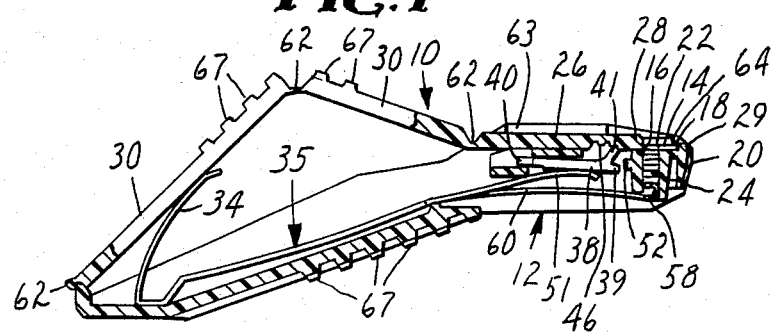
FIG. 2 is a sectional view taken approximately along line 2—2 of FIG. 1.
Figure 3:
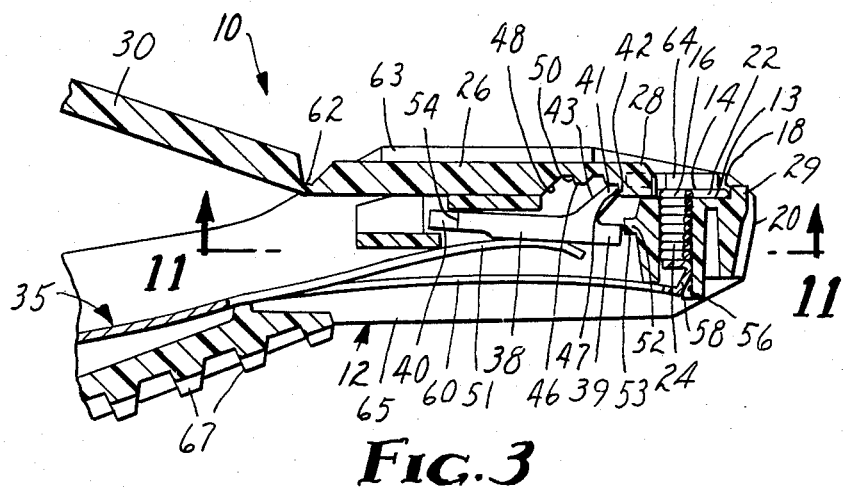
FIGS. 3 through 9 are enlarged fragmentary sectional views taken approximately along line 2—2 of FIG. 1 which sequentially show movement of a ram by a manually activated drive mechanism to form a staple and return to its initial position, and movement of a pawl for preventing reverse movement of the ram until the staple has been fully formed.
Figure 4:
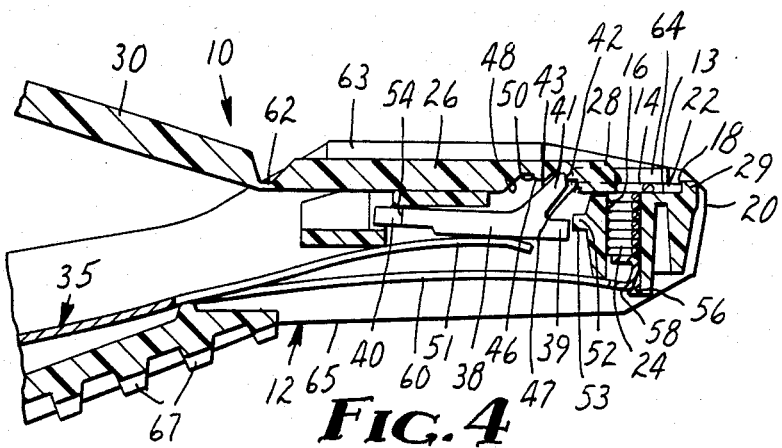
Figure 5:
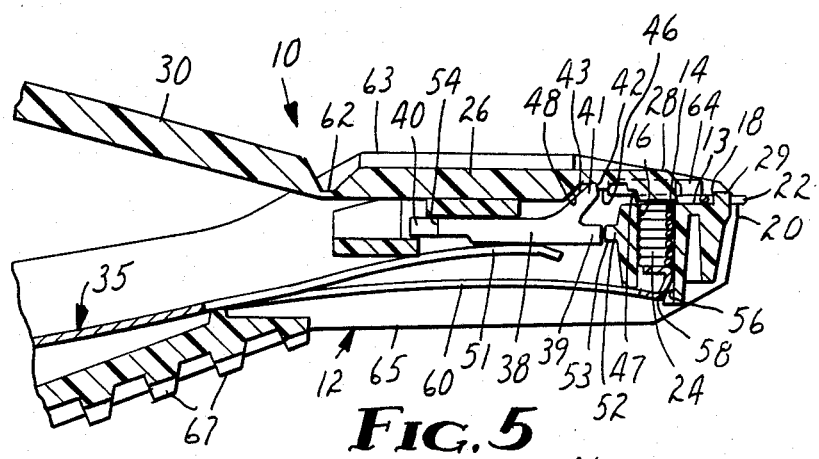
Figure 6:
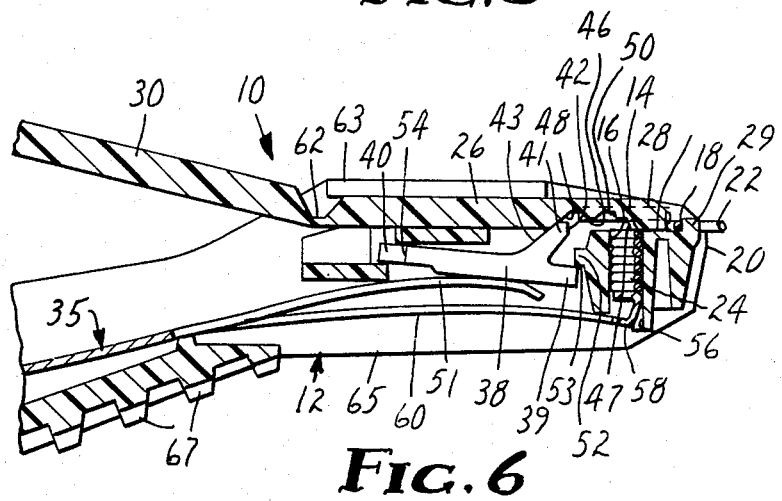
Figure 7:
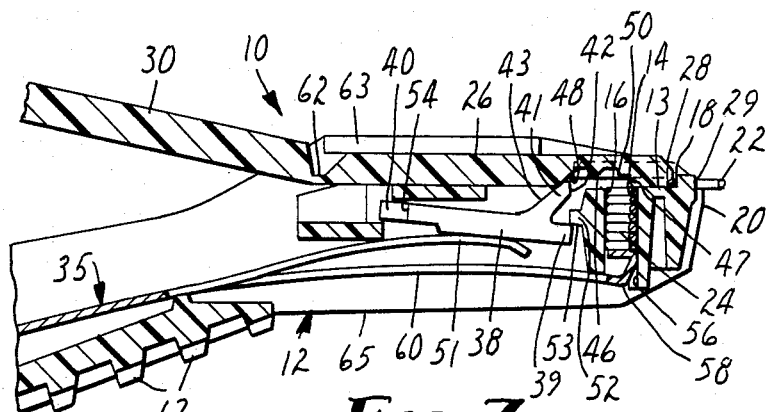
Figure 8:
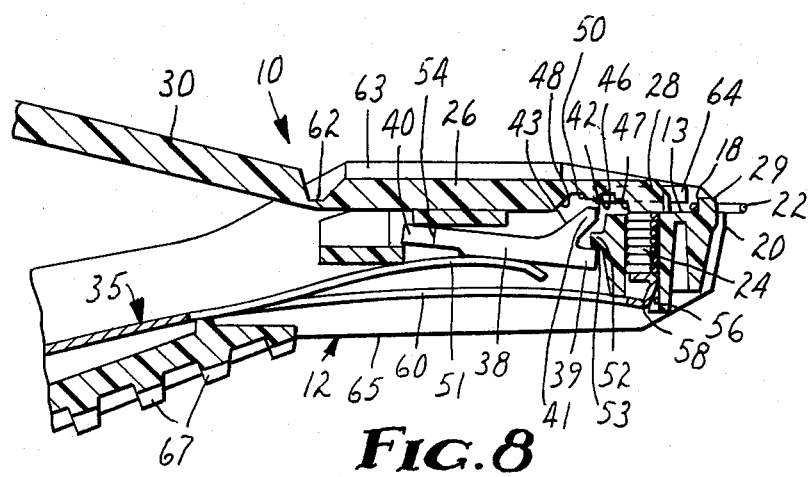
Figure 9:
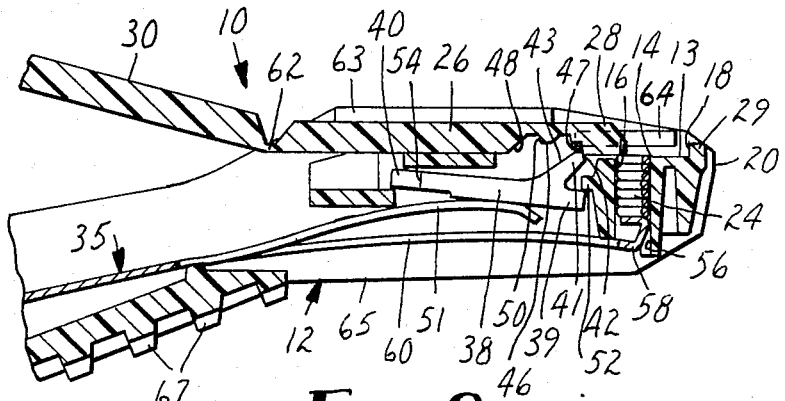
Figure 10:
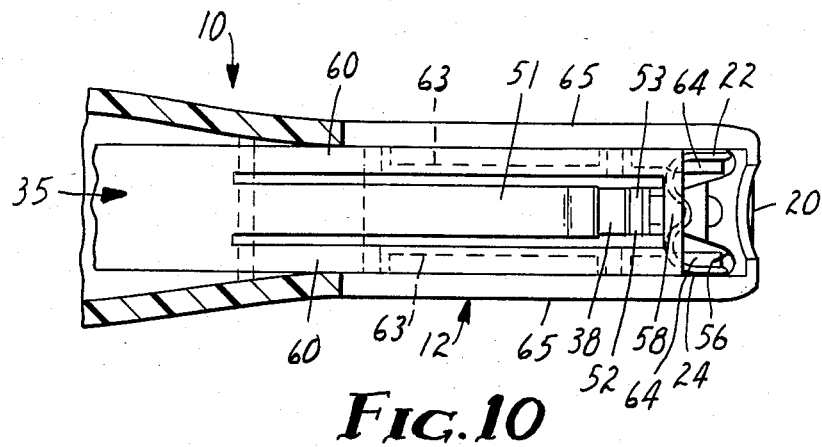
FIG. 10 is an enlarged fragmentary bottom view of the stapler shown in FIG. 1 having parts broken away to show details.
Figure 11:
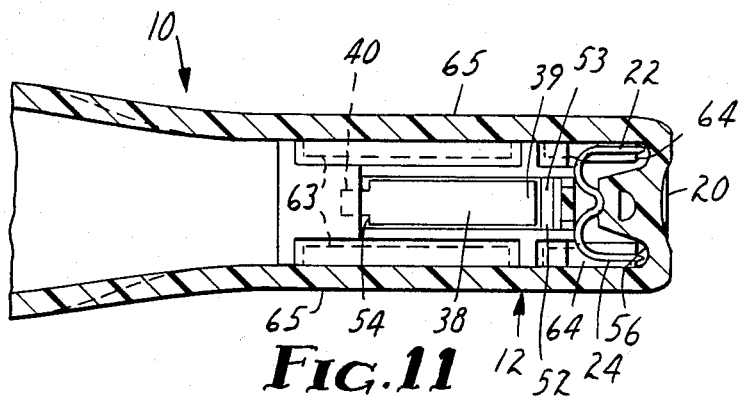
FIG. 11 is a fragmentary sectional view taken approximately along lines 11—11 of FIG. 3.

4 and 5) with the front portion 39 of the pawl 38 abutting the ledge 52 as the ram 26 moves from its load toward its eject position so that engagement between the abutment surface 42 of the tooth 41 and the latching surface 50 on one of the notches and between the shoulders 54 and the housing 12 will prevent movement of the ram 26 back toward its load position, (3) is pivoted sufficiently away from the ram 26 (FIGS. 6 and 7) so that the front portion 39 of the pawl 38 moves over and is slid along the support surface 53 of the ledge 52 to a lockout position by camming engagement between the rear surfaces 43 and 48 of the tooth 41 and recess 46 as the ram 26 moves close to its eject position, (4) is retained in the lockout position (FIG. 8) with the tooth 41 projecting into the recess 46 but out of engagement with the surfaces (including the latching surfaces 50) defining the bottom of the recess 46 as the recess 46 moves past the tooth 41 during initial movement of the ram 26 back toward its load position, and (5) is slid back to its engage position by contact between the front surface 47 of the recess 46 and the abutment surface 42 on the tooth 41 (FIG. 9) during a final portion of the rams 26 movement back to its load position (FIGS. 2 and 3).

The means for biasing the stack 24 of staples 22 into the inlet opening 16 comprises walls on the housing 12 defining a guideway 56 for the stack 24 of staples 22 leading to the inlet opening 16, and a bridge 58 joining spaced projecting portions 60 of the spring 35 (FIG. 10) flanking its central cantilevered portion 51 which bridge 58 is received in the guideway 56 to bias the stack 24 of staples 22 toward the inlet opening 16.

As is taught in U.S. patent application Ser. No. 299,068 (incorporated herein by reference), the housing 12, ram 26, and drive members 30 are made as a unitary polymeric molding with the housing 12 at one end, the ram 26 at the other, and the drive members 30 therebetween, with thin transverse connecting parts 62 of the molding pivotably joining them together. The molding is bent at the thin connecting parts 62 and front and rear portions of the ram 26 are engaged respectively between corresponding front and rear pairs of opposed lips 63 and 64 projecting toward each other from spaced side walls 65 on the housing 12 and the planar surface 13 on the housing 12 to guide the ram 26 for sliding movement between its load and eject positions, with the drive members 30 projecting away from the housing 12 to provide a single toggle joint linkage adapted to be manually pressed toward the housing 12 to move the ram 26 to its eject position to close the staple 22 around the anvil portion 29. In addition to guiding the ram 26, the surfaces of the front pair of opposed lips 64 adjacent the stack 24 of staples 22 maintain the staple 22 at the inlet opening 16 in alignment with the ram 26 in opposition to the biasing of the spring 35 when the ram 26 is in its load position, and with the opposing planar surface 13 on the housing 12 help to define the passageway 14 for guiding one of the staples 22 from the inlet opening 16 to the outlet opening 18.

The housing 12 and drive members 30 have optional transverse outwardly projecting ridges 67 on their outer surfaces which restrict slippage of the user's fingers. Also the housing 12 has a slightly concave outer surface at the ridges 67 to receive a user's thumb or finger.

A notch is centrally located across the end portion 28 of the ram 26 to receive the anvil 29 when the ram 26 is in its closed position, and the parts of the end portion 28 flanking the notch are centrally transversely grooved to receive the edge surface of the staple 22 and help keep it in alignment with the anvil portion 29 as it is closed.

A preferred polymeric material for the molding including the housing 12, ram 26, drive members 30, and thin connecting parts 62 is the polycarbonate sold under the trade designation "Lexan" by General Electric Co., Schenectady, N.Y., which provides an acceptable combination of rigidity to afford forming of the staple by pressure from its surfaces, and flexibility for the thin connecting parts 62 that allow them to be flexed without breaking for the number of times required to close a small number of the staples 22. Other polymeric materials such as nylon, polypropylene, or high density polyethylene may also be suitable, however.

The staple 22 preferably is generally W-shaped and is made of implant grade stainless steel, but could be made of other biologically acceptable metals such as some cobalt/chrome alloys. The W-shaped open staple 22 is closed to a generally D-shaped closed staple 22 as is described in U.S. Pat. No. 4,185,762 (incorporated herein by reference). In addition to the advantages with respect to the patient in which it is inserted described in U.S. Pat. No. 4,185,762, the generally W-shaped staple 22 provides the advantage of being closable with a short movement of the ram 26 which allows the use of relatively short drive members 30 and facilitates a compact design for the stapler 10; while being closable by a simple generally planar end surface on the ram 26 rather than requiring spaced staple-forming projections as are used in the stapler of U.S. Pat. No. 4,202,480, which projections might have strength problems if they were made of polymeric materials.

The one piece spring 35 provides the generally U-shaped end portion 34 that biases the ram 26 to its load position, the central cantilevered portion 51 that biases the pawl 38 toward the ram 26, and the spaced projecting portions 60 and the bridge 58 joining them that bias the stack 24 of staples 22 toward the inlet opening 16. Thus the stapler 10 (except for the staples 22) consists of only three manufactured pieces which are (1) the molding that provides the housing 12, ram 26 and drive members 30; (2) the spring 35; and (3) the pawl 38.

OPERATION

To operate the stapler 10, a user (such as a surgeon) grasps the housing 12 with his fingers, places has thumb on one of the drive members 30, and positions the end 20 of the stapler adjacent and transverse of the line between two portions of disunited tissue to be joined. The user then squeezes the drive members 30 toward the housing 12, which extends the length of the toggle joint linkage provided by the drive members 30 toward the end 20 of the stapler 10 to move the ram 26 from its load position (FIGS. 1, 2 and 3) spaced from an inlet opening 16 to the passageway 14 (which permits the top staple 22 on the stack 24 of staples 22 to be pushed into the passageway 14 by the spring portions 60) toward an eject position (FIG. 7) at which the ram 26 has closed the staple 22 around the anvil portion 29 of the housing 12 across the end of the passageway 14, causing its end portions to enter and clasp together the portions of disunited tissue (not shown).

As the ram 26 begins to move, the pawl 38 sequentially (1) is in an engage position (FIGS. 2 and 3) at which the pawl 38 is positioned when the ram 26 is in its load position with the tooth 41 in the recess 46 and the front surface 47 of the recess 46 contacting the abutment surface 42 of the tooth 41 so that the U-shaped portion 34 of the spring 35 via such contact will press the shoulders 54 on the rear portion 40 of the pawl 38 against walls on the housing 12 to define the load position for the ram 26, (2) is pivoted about the shoulders 54 to afford movement of the surfaces defining the notches at the bottom of the recess 46 along the end of the tooth 41 (FIGS. 4 and 5) with the front portion 39 of the pawl 38 abutting the ledge 52 as the ram 26 moves from its load toward its eject position so that engagement between the abutment surface 42 of the tooth 41 and the latching surface 50 on one of the notches and between the shoulders 54 and the housing 12 will prevent movement of the ram 26 back toward its load position under the influence of the U-shaped portion 34 of the spring 35 if the user releases his grip, (3) is pivoted sufficiently away from the ram 26 (FIGS. 6 and 7) so that the front portion 39 of the pawl 38 moves over and is slid along the support surface 53 of the ledge 52 to the lockout position with the tooth 41 out of engagement with the surfaces defining the bottom of the recess 46 by camming engagement between the rear surfaces 43 and 48 of the tooth 41 and recess 46 as the ram 26 moves close to its eject position, (4) is retained at the lockout position (FIG. 8) with the tooth 41 projecting into the recess 46 but out of engagement with the surfaces (including the latching surfaces 50) defining the notches at the bottom of the recess 46 as the recess 46 moves past the tooth 41 during movement of the ram 26 back to its load position, and (5) is slid back to its initial position by contact between the front surface 47 of the recess 46 and the abutment surface 42 (FIG. 9) on the tooth 41 during a final portion of the rams 26 movement back to its load position (FIGS. 2 and 3) under the influence of the U-shaped portion 34 of the spring 35.

SECOND EMBODIMENT

Figure 12:
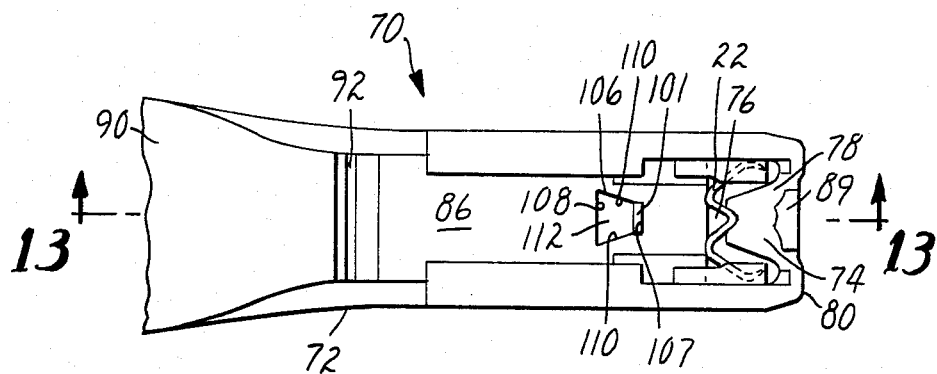
FIG. 12 is a fragmentary top view of a second embodiment of a stapler according to the present invention.
Figure 13:
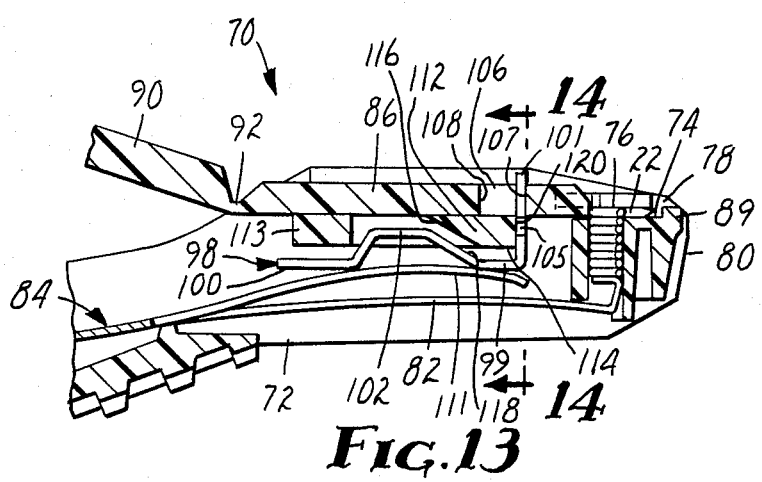
FIG. 13 is a fragmentary sectional view taken approximately along line 13—13 of FIG. 12.
Figure 14:
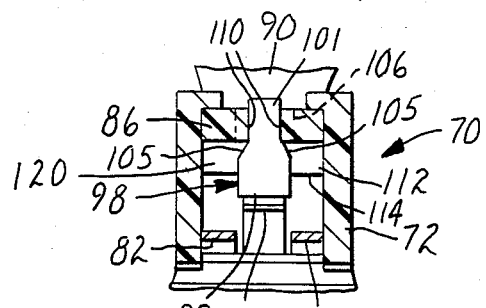
FIG. 14 is a sectional view taken approximately along line 14—14 of FIG. 13.

Referring now to FIGS. 12 through 14 of the drawing, there is shown a stapler 70 including a second embodiment of means according to the present invention for preventing double feeding of staples.

Like the stapler 10, the stapler 70 comprises a housing 72 having a passageway 74 extending from an inlet opening 76 to an outlet opening 78 at an end 80 of the housing 72, which passageway 74 is adapted to guide a single open staple 22 moved from the inlet opening 76 to the outlet opening 78; means comprising cantilevered portions 82 of a spring 84 for biasing a stack 24 of open staples 22 into the inlet opening 76; and a ram 86 mounted on the housing 12 for sliding movement (1) from a load position (FIG. 12) with the ram 86 spaced from the inlet opening 76 to afford movement of one of the open staples 22 into the passageway 74, (2) along the passageway 74 with an end portion of the ram 86 pushing the open staple 22, and (3) to an eject position at which the ram 86 has pushed the open staple 22 to the outlet opening 78 and closed the staple 22 around an anvil portion 89 of the housing 72 projecting across the outlet opening 78; after which the anvil portion 89 can be retracted from within the closed staple 22.

The ram 86 has a length adapted so that a portion of the ram 86 will always be positioned adjacent the inlet opening 76 during movement of the ram 86 from its load to its eject position to prevent movement of the adjacent staple 22 in the stack 24 into the passageway 74 through the inlet opening 76 until the staple 22 already in the passageway 74 is ejected. Drive means manually activatable by pressing a toggle joint linkage including two drive members 90 (only one of which is shown but which are disposed and connected by thin flexible transverse connecting parts 92 like the two drive members 30 in the stapler 10) toward the housing 72 is provided for propelling the ram 86 along the passageway 74 from its load to its eject position. As in the stapler 10, a generally U-shaped end portion (not shown) of the spring 84 is positioned between the housing 72 and the adjacent drive member 90 to provide means for biasing the ram 86 toward and returning the ram 86 to its load position.

Also as in the stapler 10, the means in the stapler 70 for preventing double feeding of staples 22 includes means for preventing movement of the ram 86 toward its load position from a position intermediate its load and eject positions until the ram 86 has been moved fully to its eject position which comprises a pawl 98 adapted to interact with the ram 86 and the housing 72; however, the interacting portions thereof are shaped somewhat differently. In the stapler 70, the means for preventing double feeding comprise: (1) the elongate pawl 98 which includes front, rear and central portions 99, 100 and 102 respectively, and a tooth 101 projecting from one side of the pawl 98 at an end of the front portion 99, which tooth 101 has opposite abutment edge surfaces 105 tapered toward the distal end of the tooth 101; (2) surfaces on the ram 86 defining a recess 106 adapted to receive the distal end portion of the tooth 101, which surfaces include a front surface 107 adjacent the front end 80 of the housing 72, a rear surface 108 defining the end of the recess 106 opposite the front surface 107, and latching surfaces 110 defining opposite sides of the recess 106 that are tapered toward the front surface 107 of the recess 106 and spaced so that the recess 106 can receive the end portion of the tooth 101 with the abutment edge surfaces 105 of the tooth 101 in contact with the latching surfaces 110; and (3) mounting means mounting the pawl 98 on the housing 72 generally parallel with the ram 86 with its front portion 99 adjacent the end 80 of the housing 72 and its tooth 101 in the recess 106 in the ram 86 for longitudinal sliding and transverse movement. These mounting means comprise means for biasing the tooth 101 toward the recess 106 provided by a central cantilevered portion 111 of the spring 84, and spaced front and rear support members 112 and 113 formed on the housing 72 extending generally transverse to the ram 86, with the front support member 112 being closest to the end 80 of the housing 72 and having a support surface 114 on its side opposite the ram 86. The pawl 98 has spaced recesses adjacent its front and rear portions 99 and 100 adapted to receive the support members 112 and 113 when the pawl 98 is in an engage position (FIGS. 12 and 13) at which the abutment edge surfaces 105 on the tooth 101 can be biased into engagement with the latching surfaces 110 along the recess 106; and at least a rear surface 116 on the front support member 112 or a front surface 118 on the central portion 102 of the pawl 98 (and as illustrated, both surfaces 116 and 118) are inclined to cam the central portion 102 of the pawl 98 onto the support surface 114 on the front support member 112 and thus move the tooth 101 transversely partially out of the recess 106 when the pawl 98 is moved to a lockout position toward the front end 80 of the housing 72. During movement of the ram 86 from its load to its eject position and back to its load position, the pawl 98 sequentially (1) is first in its engage position (FIGS. 12 and 13) with the tooth 101 in the recess 106 contacting its front surface 107 and contacting a front edge surface 120 of the front support member 112 to define the load position for the ram 86, (2) moves transversely toward the ram 86 deeper into the recess 106 with the tapered abutment surfaces 105 on the tooth 101 moving along the latching surfaces 110 defining the sides of the recess 106 as the ram 86 moves through the major portion of its travel from its load toward its eject position, with engagement between the abutment and latching surfaces 105 and 110 and between the tooth 101 and the front edge surface 120 of the front support member 112 preventing movement of the ram 86 back toward its load position, (3) is moved to its lockout position by engagement between the rear surface 108 of the recess 106 and the tooth 101 which carries the pawl 98 with the ram 86 as the ram 86 moves the final portion of its travel to its eject position, thereby causing camming engagement between the front surface 118 of the central portion 102 and rear surface 116 of the front support member 112 to move the central portion 102 of the pawl 98 onto the support surface 114 and the tooth 101 sufficiently transversely away from the ram 86 so that the abutment edge surfaces 105 of the tooth 101 and the latching surfaces 110 along the recess 106 are separated, (4) is retained in the lockout position with the tooth 101 projecting into the recess 106 but with its abutment surfaces 105 out of engagement with the side latching surfaces 110 defining the recess 106 as the recess 106 moves past the tooth 101 during the initial major portion of the movement of the ram 86 back toward its load position, and (5) is slid back to its engage position by contact between the front surface 107 of the recess 106 and the tooth 101 during a final portion of the ram's 86 movement back to its load position.

The present invention has now been described with reference to two embodiments thereof. It will be understood that either embodiment 10 or 70 disclosed herein may be subject to many modifications and alterations without departing from the spirit of the invention. For example, the end of the rams could be made of metal and could be shaped like the end of the ram in U.S. Pat. No. 4,202,480, and generally U-shaped staples could be applied with the stapler; or the body, ram, and the members forming the toggle joint linkage could be separate, and could be joined by conventional hinge pin structures or by flexible connecting material such as tape; or an entirely different drive mechanism could be used to propel the ram such as pliers-like handles similar to those used in U.S. Pat. No. 3,873,016. Also the abutment and latching surfaces may take different shapes, for example, the latching surfaces in either embodiment could be incorporated in a generally stair-step shaped structure either along the bottom of a recess for engagement by an abutment surface at the end of a tooth, or along the edges of a tapered recess for engagement by opposite tapered abutment surfaces. Thus the scope of the present invention should not be limited by the structures of the embodiments disclosed, but only by the structures described by language of the claims and their equivalents.

I claim:

1. In a stapler comprising:
    a housing having a passageway extending from an inlet opening to an outlet opening, said openings and passageway being adapted to guide a single open staple moved from the inlet to the outlet opening;
    means for biasing a stack of staples into said inlet opening;
    a ram having an end portion adapted to engage a said staple and being mounted on said housing for sliding movement between a load position with the ram spaced from the inlet opening to afford movement of one of the staples into the passageway, along said passageway with said end portion pushing the staple, to an eject position at which the end portion of the ram has pushed the staple to said outlet opening; said ram having a length adapted so that a portion thereof will be positioned adjacent said inlet opening during movement of said ram from said load to said eject position to prevent movement of a second staple into said passageway through said inlet opening;
    drive means adapted for manual activation to move said ram along said passageway, thereby moving one of the staples from said inlet opening through said passageway and to said outlet opening; and
    means for biasing said ram toward said load position, the improvement wherein:
    said stapler includes antireverse means for preventing movement of said ram toward said load position from a position intermediate said load and eject positions until said ram has been moved fully to said eject position, said antireverse means comprising:
    an elongate pawl including front and rear portions, and a tooth projecting from one side;
    surfaces on said ram defining an elongate recess adapted to receive said tooth, said surfaces including a front surface adjacent the end portion of said ram and a rear surface defining the end of said recess opposite said front surface;
    mounting means mounting said pawl on said housing generally parallel with said ram with said front portion adjacent said outlet opening and said tooth in said recess for longitudinal sliding movement relative to said housing, from (1) an engage position at which said pawl is positioned with the front surface of the recess contacting said tooth when said ram is in said load position and at which the pawl is positioned during movement of said ram a substantial portion of the distance toward said eject position until said rear surface of said recess contacts said tooth, (2) to a lockout position more closely adjacent said outlet opening than said initial position to which said pawl is moved by contact between said rear surface and said tooth during a final portion of the movement of said ram to said eject position and at which the pawl is maintained during a major portion of the movement of the ram back to the load position, and (3) back to said engage position to which said pawl is moved by contact between said front surface and said tooth during the final portion of movement of said ram from said eject back to said load position;
    means for biasing said tooth toward said recess;
    surface means including at least one abutment surface on said tooth and latching surfaces defining said recess between said front and rear surfaces for affording, when said abutment and latching surfaces are in engagement, movement of said ram toward said eject position while preventing movement of said ram toward said load position; and
    means for affording engagement of the abutment surface of said tooth with the latching surface of said recess under the influence of said biasing means when said pawl is in said engage position, for moving said abutment and latching surfaces out of engagement as said pawl is moved from said engage to said lockout position, and for maintaining said abutment and latching surfaces out of engagement when said pawl is in said lockout position.

2. A stapler according to claim 1 wherein said tooth on said pawl projects from between said front and rear portions, said abutment surface on said tooth is adjacent said front portion, and said tooth has a rear surface adjacent said rear portion;

said means for maintaining said abutment and latching surfaces out of engagement when said pawl is in said lockout position comprises a ledge formed on said housing projecting generally parallel to said ram away from said outlet opening and having a support surface on its side opposite said ram adapted to engage and support said front portion of said pawl in opposition to said means for biasing when said pawl is in said lockout position; and said means for moving said abutment and latching surfaces out of engagement comprises at least the rear surface on said tooth or the rear surface defining said recess being oriented to cam said tooth partially out of said recess when the rear surface defining said recess contacts and moves toward said tooth.

3. A stapler according to claim 2 wherein said latching surfaces define a plurality of ratchet teeth along the bottom of said recess.

4. A stapler according to claim 1 wherein said means for maintaining said abutment and latching surfaces out of engagement when said pawl is in said lockout position comprises at least one support member formed on said housing, extending transverse of said ram between said pawl and said ram and having a support surface on its side opposite said ram; said pawl has a recess adapted to receive said support member, said recess being positioned adjacent said support member when said pawl is in said engage position, and has a portion adjacent said recess adapted to be positioned adjacent and supported by the support surface in opposition to said means for biasing when said pawl is in said lockout position; and said means for moving said abutment and latching surfaces out of engagement comprises at least one surface on said support member or on said pawl which is oriented to cam the tooth partially out of said recess and said portion adjacent said recess onto said support surface as said pawl is moved from said engage to said lockout position.

5. A stapler according to claim 4 wherein said latching surfaces define opposite sides of said recess and are tapered toward toward said front surface, and said tooth has opposite abutment surfaces defined by opposed sides of said tooth tapered toward the distal end of said tooth so that said tooth will be moved farther into said recess by said biasing means during movement of said ram from from said load toward said eject position.

6. In a stapler comprising:
a housing having a passageway extending from an inlet opening to an outlet opening, said openings and passageway being adapted to guide a single open staple moved from the inlet to the outlet opening;
means for biasing a stack of open staples into said inlet opening;
a ram having an end portion adapted to engage a said staple and being mounted on said housing for sliding movement between a load position with the ram spaced from the inlet opening to afford movement of one of the staples into the passageway, along said passageway with said end portion pushing the staple, to an eject position at which the end portion of the ram has pushed the staple to said outlet opening; said ram having a length adapted so that a portion thereof will be positioned adjacent said inlet opening during movement of said ram from said load to said eject position to prevent movement of a second staple into said passageway through said inlet opening;
drive means adapted for manual activation to move said ram along said passageway, thereby moving one of the staples from said inlet opening through said passageway and to said outlet opening; and
means for biasing said ram toward said load position, the improvement wherein:
said stapler includes an antireverse means for preventing movement of said ram toward said load position from a position intermediate said load and eject positions until said ram has been moved fully to said eject position, said antireverse means comprising:
an elongate pawl including front and rear portions, and a tooth projecting from one side between said front and rear portions, said tooth having an abutment surface adjacent said front portion and a rear surface adjacent said rear portion;
surfaces on said ram defining a recess adapted to receive said tooth, said surfaces including a front surface adjacent the end portion of said ram adapted to abut the abutment surface of said tooth, a rear surface defining the end of said recess opposite said front surface, and latching surfaces between said front and rear surfaces; and
mounting means mounting said pawl on said housing generally parallel with said ram with said front portion adjacent said outlet opening and said tooth in the recess in said ram for longitudinal slidable and pivotal movement, said mounting means comprising:
means for biasing said tooth toward said recess; and
a ledge formed on said housing projecting generally parallel to said ram away from said outlet opening and having a support surface on its side opposite said ram;
said abutment surface and latching surfaces defining said recess between said front and rear surfaces being adapted for engagement when biased together to afford movement of said rear surface toward said tooth while restricting movement of said front surface toward said tooth, and at least the rear surface on said tooth or the rear surface defining said recess being oriented to cam said tooth partially out of said recess when the rear surface defining said recess contacts and moves toward said tooth so that said pawl sequentially (1) is in an engage position at which said pawl is positioned when said ram is in said load position with said tooth in said recess and the front surface of the recess contacting the abutment surface of said tooth (2) pivots to move along said recess with said front portion of the pawl abutting said ledge as said ram moves from said load toward said eject position so that engagement between said abutment surface of the tooth and said latching surface and between the pawl and the housing will prevent movement of said ram back toward said load position, (3) is pivoted sufficiently away from said ram so that said front portion of the pawl moves over and is slid along the support surface of said ledge to a lockout position with said abutment and latching surfaces out of engagement by camming engagement between said rear surfaces of said tooth and recess as said ram moves close to said eject position, (4) is retained at the lockout position with said tooth projecting into the recess but with said abutment and latching surfaces out of engagement as the recess moves past said tooth during the major portion of movement of said ram back to its load position, and (5) is slid back to its engage position by contact between said front surface of the recess and said abutment surface on the tooth during a final portion of the ram's movement back to said load position.

7. A stapler according to claim 6 wherein said latching surfaces are transverse of and at the bottom of said recess.

* * * * *